(12) United States Patent
Poupyrev et al.

(10) Patent No.: US 11,151,857 B2
(45) Date of Patent: *Oct. 19, 2021

(54) ERGONOMIC ASSESSMENT GARMENT (71) Applicant: Google LLC, Mountain View, CA (US)

(72) Inventors: Ivan Poupyrev, Sunnyvale, CA (US);
Antonio Xavier Cerruto, Menlo Park, CA (US); Mustafa Emre Karagozler, Mountain View, CA (US); David Scott Allmon, Sunnyvale, CA (US); Munehiko Sato, Tokyo (JP); Susan Jane Wilhite, Pacifica, CA (US); Shiho Fukuhara, Mountain View, CA (US)

(73) Assignee: Google LLC, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/827,024

(22) Filed: Mar. 23, 2020

(65) Prior Publication Data
US 2020/0258366 A1 Aug. 13, 2020

Related U.S. Application Data (63) Continuation of application No. 16/446,008, filed on Jun. 19, 2019, now Pat. No. 10,600,304, which is a
(Continued)

(51) Int. Cl.
G08B 23/00 (2006.01)
G08B 21/04 (2006.01)
(Continued)

(52) U.S. Cl.
CPC ........ G08B 21/0446 (2013.01); A61B 5/1114 (2013.01); A61B 5/1116 (2013.01);
(Continued)

(58) Field of Classification Search
CPC .... G08B 21/0446; G16H 50/20; G16H 40/63; A61B 5/114; A61B 5/1116; A61B 5/1121; A61B 5/6804; A61B 5/0022
See application file for complete search history.

(56) References Cited

U.S. PATENT DOCUMENTS

| 5,398,019 A | 3/1995 | Barnett et al. |
| 2007/0089800 A1 | 4/2007 | Sharma |

(Continued)

FOREIGN PATENT DOCUMENTS

| CN | 105474166 | 4/2016 |
| JP | 2014217753 | 11/2014 |

(Continued)

OTHER PUBLICATIONS

Cho et al., "Performance Evaluation of Textile-Based Electrodes and Motion Sensors for Smart Clothing", IEEE Sensors Journal, vol. 11, No. 12, Dec. 2011, pp. 3181-3193.

(Continued)

Primary Examiner — Phung Nguyen
(74) Attorney, Agent, or Firm — Dority & Manning, P.A.

(57) ABSTRACT

Systems and methods of determining an ergonomic assessment for a user are provided. For instance, sensor data can be received from one or more sensors implemented with an ergonomic assessment garment worn by a user. Corporeal data associated with at least one body segment of the user can be determined based at least in part on the sensor data. The corporeal data is associated with a bend angle associated with the at least one body segment. An ergonomic assessment associated with the user can be determined based at least in part on the corporeal data. The ergonomic assessment can include an indication of one or more ergonomic zones associated with the user, the one or more ergonomic
(Continued)

zones being determined based at least in part on the bend angle associated with the at least one body segment.

20 Claims, 3 Drawing Sheets

Related U.S. Application Data continuation of application No. 15/570,461, filed as application No. PCT/US2017/017009 on Feb. 8, 2017, now Pat. No. 10,366,593.

(51) Int. Cl.

| | |
|---|---|
| *G16H 40/63* | (2018.01) |
| *G16H 50/20* | (2018.01) |
| *A61B 5/11* | (2006.01) |
| *A61B 5/00* | (2006.01) |
| *A61B 5/024* | (2006.01) |
| *A61B 5/389* | (2021.01) |

(52) U.S. Cl.
CPC .......... *A61B 5/1121* (2013.01); *A61B 5/6804* (2013.01); *G16H 40/63* (2018.01); *G16H 50/20* (2018.01); *A61B 5/0022* (2013.01); *A61B 5/02438* (2013.01); *A61B 5/389* (2021.01); *A61B 5/7264* (2013.01); *A61B 5/7455* (2013.01); *A61B 2562/0219* (2013.01)

(56) References Cited

U.S. PATENT DOCUMENTS

| | | | |
|---|---|---|---|
| 2009/0204031 A1 | 8/2009 | McNames et al. | |
| 2010/0185076 A1 | 7/2010 | Jeong et al. | |
| 2012/0179011 A1 | 7/2012 | Moon et al. | |
| 2014/0135593 A1* | 5/2014 | Jayalth ................ | A61B 5/318 |
| | | | 600/301 |
| 2014/0238151 A1* | 8/2014 | Dunne ................. | G01L 1/2287 |
| | | | 73/862.474 |
| 2015/0045700 A1 | 2/2015 | Cavanagh et al. | |
| 2015/0057984 A1* | 2/2015 | Nicoletti .............. | A61B 5/6804 |
| | | | 703/2 |
| 2015/0190669 A1 | 7/2015 | Matsuura et al. | |
| 2016/0199685 A1* | 7/2016 | von Hoffmann .. | A63B 21/4017 |
| | | | 482/8 |
| 2016/0279475 A1 | 9/2016 | Aragones et al. | |
| 2016/0317089 A1 | 11/2016 | Pyfe et al. | |
| 2016/0338621 A1 | 11/2016 | Kanchan et al. | |
| 2016/0338644 A1* | 11/2016 | Connor ................ | A61B 5/1071 |
| 2017/0196513 A1 | 7/2017 | Longinotti-Buitoni et al. | |
| 2017/0274249 A1 | 9/2017 | Moebius et al. | |
| 2018/0140902 A1* | 5/2018 | Wiebe .................. | A61B 5/1118 |

FOREIGN PATENT DOCUMENTS

| | | |
|---|---|---|
| WO | WO 2009/112281 | 9/2009 |
| WO | WO 2015/138515 | 9/2015 |
| WO | WO 2016/123654 | 8/2016 |
| WO | WO2017010236 | 1/2017 |

OTHER PUBLICATIONS

International Search Report for PCT/US2017/017009 dated Jan. 2, 2018, 6 pages.
Langereis et al., "ConText: Contactless Sensors for Body Monitoring Incorporated in Textiles", International Conference on Portable Information Devices, May 25-29, 2007, Orlando, Florida, 5 pages.
Lymberis et al., "Intelligent Biomedical Clothing for Personal Health and Disease Management: State of the Art and Future Vision", Telemedicine Journal and e-Health, vol. 9, No. 4, 2003, pp. 379-386.
Frisoli et al., "Preliminary Design of Rowing Simulator for In-Door Skill Training" 2008 ICST, Feb. 14, 2008, pp. 1-20.
Sklubewska-Paszkowska et al., "Motion Capture as a Modern Technology for Analysing Ergometer Rowing", Advances in Science and Technology, Mar. 29, 2016, pp. 132-139.

* cited by examiner

ERGONOMIC ASSESSMENT GARMENT

PRIORITY CLAIM

The present application is a continuation of U.S. application Ser. No. 16/446,008, having a filing date of Jun. 19, 2019 and now issued as U.S. Pat. No. 10,600,304, which is a continuation of U.S. application Ser. No. 15/570,461, having a filing date of Oct. 30, 2017 and now issued as U.S. Pat. No. 10,366,593, which is based upon and claims the right of priority under 35 U.S.C. § 371 to International Application No. PCT/US2017/017009, having a filing date of Feb. 8, 2017. Applicant claims priority to and the benefit of each of such applications and incorporates all such applications herein by reference in their entirety.

FIELD

The present disclosure relates generally to determining ergonomic assessments associated with a user.

BACKGROUND

Current techniques for measuring posture and motion of a person rely on methods that are coarse and imprecise (e.g. visual observation and estimation), or that are intrusive and involve cumbersome or unwieldy instrumentation (e.g. goniometers). Such techniques, although sufficient in some cases, can be inaccurate and/or difficult to implement. For instance, it can be difficult to obtain posture and/or motion information associated with a factory worker performing routine tasks due to the cumbersome and unwieldy nature of instrumentation used to obtain such information.

SUMMARY

Aspects and advantages of embodiments of the present disclosure will be set forth in part in the following description, or may be learned from the description, or may be learned through practice of the embodiments.

One example aspect of the present disclosure is directed to a computer-implemented method of determining an ergonomic assessment associated with a user. The method includes receiving, by one or more computing devices, sensor data from one or more sensors implemented with an ergonomic assessment garment worn by a user. The method further includes determining, by the one or more computing devices, corporeal data associated with at least one body segment of the user based at least in part on the sensor data. The corporeal data is associated with a bend angle associated with the at least one body segment. The method further includes determining, by the one or more computing devices, an ergonomic assessment associated with the user based at least in part on the corporeal data. The ergonomic assessment includes an indication of one or more ergonomic zones associated with the user. The one or more ergonomic zones are determined based at least in part on the bend angle associated with the at least one body segment.

Other example aspects of the present disclosure are directed to systems, apparatus, tangible, non-transitory computer-readable media, user interfaces, memory devices, and electronic devices for determining ergonomic assessments for a user.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE DRAWINGS

Detailed discussion of embodiments directed to one of ordinary skill in the art are set forth in the specification, which makes reference to the appended figures, in which.

DETAILED DESCRIPTION

Reference now will be made in detail to embodiments, one or more examples of which are illustrated in the drawings. Each example is provided by way of explanation of the embodiments, not limitation of the present disclosure. In fact, it will be apparent to those skilled in the art that various modifications and variations can be made to the embodiments without departing from the scope or spirit of the present disclosure. For instance, features illustrated or described as part of one embodiment can be used with another embodiment to yield a still further embodiment. Thus, it is intended that aspects of the present disclosure cover such modifications and variations.

Example aspects of the present disclosure are directed to determining ergonomic assessments using an ergonomic assessment garment capable of being worn by a user. For instance, sensor data can be received from one or more sensors implemented with the ergonomic assessment garment worn by the user. Corporeal data associated with one or more body segments of the user can be determined based at least in part on the sensor data. The corporeal data can include data associated with a bend angle of at least one body segment of the user, a bend speed of at least one body segment of the user, an acceleration of the bend of at least one body segment of the user, a duration of motion associated with the user, and/or a repetitive nature of motion. An ergonomic assessment can be determined based at least in part on the corporeal data. The ergonomic assessment can comprise an indication of one or more ergonomic zones in which the user is placed based at least in part on the bend angle associated with the at least one body segment.

More particularly, the ergonomic assessment garment can be any suitable garment configured to be worn by a user and to monitor data associated with the motion and/or posture of the user. In some implementations, the ergonomic assessment garment can be an upper body garment, such as a shirt, jacket, sweater, etc. In this manner, the ergonomic assessment garment can be loose fitting similar to a typical upper body garment, and is not required to be form fitting to the user. The ergonomic assessment garment can be implemented with one or more sensor devices configured to monitor data associated with the motion and/or posture of the user while being worn by the user. For instance, the sensors can be integrated within the fabric of the ergonomic assessment garment, or otherwise attached to the ergonomic assessment garment. Such sensors can include one or more accelerometers, gyroscopes, inertial measurement units, force gauges, tachometers, electromyography sensors, heart rate monitors, and/or other suitable sensors capable of measuring physiological data associated with a user's movement and/or posture.

In some implementations, the ergonomic assessment garment can be a smart garment constructed using a plurality of electrically conductive yarns. For instance, the electrically conductive yarns can be woven into the fabric structure of the garment to form one or more circuits. In some implementations, the electrically conductive yarns can be combined with non-conductive yarns to construct the ergonomic assessment garment. In such implementations, the garment can include a fabric that has the feel, drape characteristics, and other properties of typical fabrics used to produce garments and the like. Thus, the electrically conductive yarns can be incorporated into the fabric of the ergonomic assessment garment without undesirably increasing stiffness or imparting any other undesirable characteristics into the fabric.

In such implementations, the one or more sensors of the ergonomic assessment garment can be coupled to one or more electrically conductive yarns to form one or more circuits. For instance, the electrically conductive yarns can be arranged to electrically couple the one or more sensors to one or more processing devices configured to implement various example aspects of the present disclosure.

The sensor data can be used to determine corporeal data associated with the user. For instance, such corporeal data can include data associated with a bend angle of one or more joints or body segments of the user. For instance, the corporeal data can include data indicative of a bend angle of a user's shoulder, elbow, back, neck, knees, etc. In some implementations, the corporeal data can include data associated with a range of motion of the one or more body segments, a velocity of motion of the one or more body segments, an acceleration of motion of the one or more body segments, and/or other suitable corporeal data associated with the motion and/or posture of the user. In some implementations, the corporeal data can include data indicative of a timing of the bend angle(s) of the one or more body segments. In some implementations, the corporeal data can include relative bend angles (e.g. relative to one or more bend angle thresholds). In some implementations, the corporeal data can include data indicative of a number of times within a particular time period that a particular body segment was bent at an angle greater than the corresponding bend angle threshold for the body segment. Additionally, or alternatively, the corporeal data can include behavior data. The behavior data can be indicative of a job activity performed, productivity estimates (e.g., number of towels folded per minute).

Such corporeal data can be used in determining an ergonomic assessment associated with the user. The ergonomic assessment can include various attributes associated with the motion and/or posture of the user. For instance, the motion and/or posture of the user can be categorized into one or more ergonomic zones associated with the posture and/or motion of the user during one or more time periods. The ergonomic zones can specify various qualities of the posture and/or motion of the user during the one or more time periods. Each subject body segment (e.g. shoulders, back, knees, etc.) can have a plurality of associated ergonomic zones in which the motion and/or posture of the body segment can be categorized. The ergonomic zones can be defined based at least in part on a bend angle threshold associated with the subject body segment. In some implementations, each zone can be defined based at least in part on a number of times in which the bend angle of the subject body segment is greater than the threshold during one or more time periods. For instance, a first zone can indicate that, on average, the bend angle of the subject body segment was greater than the threshold less than one time per minute (or other suitable period) during a measurement period. A second zone can indicate that, on average, the bend angle of the subject body part was greater than the threshold between one and two time per minute during the measurement period. A third zone can indicate that, on average, the bend angle of the subject body part was greater than the threshold more than two times per minute during the measurement period. In this manner, the first zone can indicate a higher quality of posture and/or motion than the second and third zones. In such implementations, the bend angle of the subject body part can be monitored throughout a plurality of periodical blocks (e.g. one minute blocks) of time during a measurement period.

In some implementations, the ergonomic zones can be determined based at least in part on a ratio of time during which the bend angle of the subject body segment was greater than the threshold during the measurement period. For instance, a first zone can indicate that the bend angle of the subject body segment was greater than the threshold for less than ⅕ (or other suitable ratio) of the measurement period. A second zone can indicate that the bend angle of the subject body segment was greater than the threshold between ⅕ and ⅓ of the measurement period. A third zone can indicate that the bend angle of the subject body segment was greater than the threshold for more than ⅓ of the measurement period. In this manner, the first zone can indicate a higher quality of posture and/or motion for the subject body segment that the second and third zones.

In some implementations, the ergonomic zones can be determined based at least in part on a speed and/or acceleration of motion of a subject body segment. For instance, the zones can be defined based at least in part on a threshold of acceleration or speed. More particularly, the ergonomic zones can be defined based at least in part on a number of times during which the speed and/or acceleration of the subject body segment is greater than the threshold and/or a ratio of time during which the speed and/or acceleration is greater than the threshold.

It will be appreciated that the example ergonomic zones described above are intended for illustrative purposes only. More particularly, it will be appreciated that any suitable metric for defining one or more ergonomic zones can be used without deviating from the scope of the present disclosure. For instance, the ergonomic zones can be defined based on any combination of one or more suitable bend angle thresholds, speed thresholds, acceleration thresholds, number of times wherein the bend angle, acceleration, speed, etc. of the subject body segment is greater than the corresponding threshold(s), ratio of time wherein the bend angle, acceleration, speed, etc. of the subject body segment is greater than the corresponding threshold(s), etc.

In some implementations, the ergonomic assessment can specify an overall ergonomic zone in which the user is categorized. The overall ergonomic zone can be determined based at least in part on one or more ergonomic zones determined during a measurement period for one or more subject body segments. For instance, if ergonomic zones for multiple subject body segments are determined during a measurement period, then the overall ergonomic zone can be determined based at least in part on each ergonomic zone determined for each subject body segment. In some implementations, the overall ergonomic zone can correspond to the ergonomic zone for the subject body segment indicating the lowest quality of posture and/or motion.

The ergonomic assessment can further include a power expenditure metric for one or more subject body segments. A power expenditure metric can provide an estimated amount of power generated by a subject body segment during a measurement period. For instance, the power expenditure metric can be determined based at least in part on a speed and/or acceleration of motion, a range of motion and/or other parameter associated with a one subject body segment. In some implementations, the ergonomic assessment can include an overall power expenditure metric specifying an aggregation of the power expenditure metrics for each subject body segment. The power expenditure metrics can be determined relative to a maximum power expenditure value. The maximum value can be any suitable value specifying a maximum suitable amount of power that can be safely expended by a user. In some implementations, the maximum value can be personalized to the individual user.

The ergonomic assessment can further include a productivity assessment that can indicate monitored periods of work, periods of rest, number of rests (e.g. average number of rests), duration of rests (e.g. average duration of rests), types of work being performed, an estimated quantity of output per unit time for certain job functions, and/or any other suitable productivity measures. Such productivity assessment can be determined from the sensor data and/or the corporeal data. For instance, the sensor data can be used to determine when the user is active and when the user is working. The sensor data can further be used to categorize the type of work being performed by the user.

In some implementations, the ergonomic assessment can be used to provide haptic feedback to the user. For instance, one or more haptic feedback devices (e.g. vibratory motors, actuators, etc.) can be implemented with the ergonomic assessment garment. Such feedback devices can be used to provide haptic feedback to the user based at least in part on the ergonomic assessment. The haptic feedback can be provided to indicate information relating to the posture and/or motion data of the user. For instance, haptic feedback can be provided to the user to indicate that the motion and/or posture of the user corresponds to a particular ergonomic zone, to indicate that the user is expending too much power, etc.

The ergonomic assessment can be provided to the user or other entity, for instance, via a user device (e.g. smartphone, tablet, laptop, desktop, smartwatch, fitness band, etc.) associated with the user. In this manner, the ergonomic assessment can provide to the user or other entity a report specifying information associated with the user's posture and/or motion during one or more measurement periods. In some implementations, ergonomic assessments of a plurality of users can be provided to one or more remote computing devices (e.g. server devices) to determine broader trends regarding the posture and/or motion habits of the plurality of users.

Figure 1:
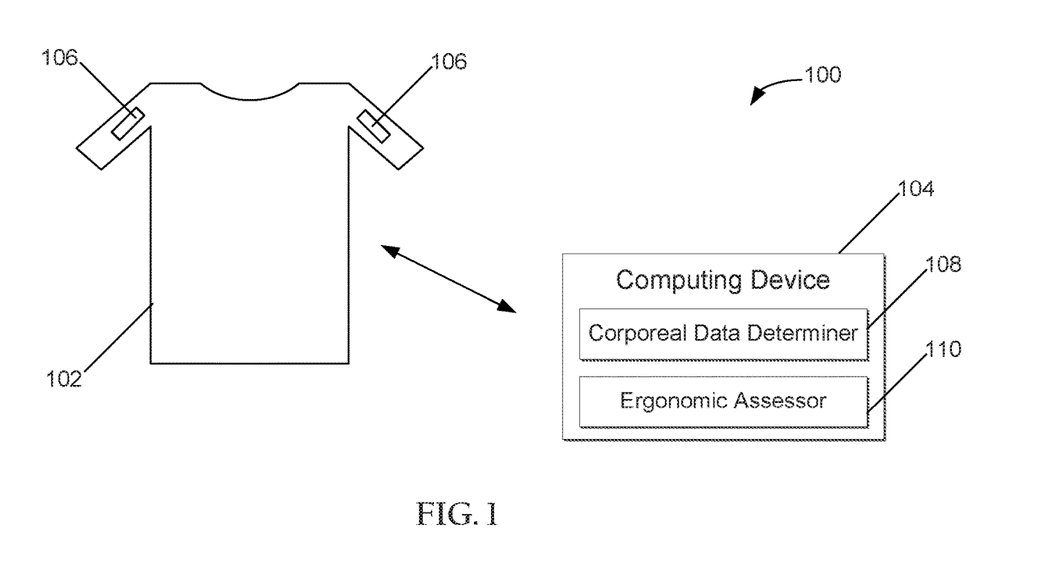
FIG. 1 depicts an example system for determining ergonomic assessments for a user according to example aspects of the present disclosure.

With reference now to the figures, example aspects of the present disclosure will be provided in greater detail. For instance, FIG. 1 depicts an example system 100 for determining an ergonomic assessment associated with a user in accordance with example aspects of the present disclosure. The system 100 includes an ergonomic assessment garment 102 and a computing device 104. In some implementations, the computing device 104 can be integrated or implemented within, or otherwise attached to the ergonomic assessment garment 102. In some implementations, the computing device 104 can be a separate and distinct device from the ergonomic assessment garment 102. In such implementations, the computing device 104 may be communicatively coupled to the ergonomic assessment garment 102, for instance, via a network. For instance, in such implementations, the computing device 104 can be a self-contained device and can be attached, affixed, or otherwise connected to any suitable garment worn by a user.

The ergonomic assessment garment 102 can include one or more sensor devices 106. The sensor devices 106 can be configured to measure data indicative of the motion and/or posture of a user wearing the ergonomic assessment garment 102. The sensor devices 106 can include one or more accelerometers, gyroscopes, inertial measurement units, force gauges, tachometers, electromyography sensors, heart rate monitors, and/or other suitable sensors capable of measuring data associated with a user's movement and/or posture. Although only two sensor devices 106 are depicted in FIG. 1, it will be appreciated that the ergonomic assessment garment 102 can include any suitable number of sensor devices. In addition, although the sensor devices 106 are positioned on the sleeves of the ergonomic assessment garment 102 (proximate the user's shoulders), it will be appreciated that the sensor devices 106 can be positioned in any suitable manner with respect to the ergonomic assessment garment 102 to facilitate the measurement of the desired motion and/or posture data associated of the user.

In some implementations, the ergonomic assessment garment 102 can be a smart garment constructed using one or more electrically conductive yarns. In such implementations, the sensor devices 106 can be coupled to such electrically conductive yarns to form circuits that implement example aspects of the present disclosure. For instance, the sensor devices 106 can be coupled to each other via such electrically conductive yarns. In some implementations, the sensor devices 106 can be coupled to computing device 104 and/or other suitable computing device via the electrically conductive yarns.

The ergonomic assessment garment 102 can include a fabric structure generally formed from yarns that are woven or knitted together. In implementations wherein the ergonomic assessment garment 102 is a smart garment, at least certain of the yarns are electrically conductive. The electrically conductive yarns can be woven into the fabric structure in order to form various different electronic circuits. Various different types of electrical devices can be attached to the yarns and controlled by a controller, such as a microprocessor. In one embodiment, the entire fabric structure can be made from electrically conductive yarns. In an alternative embodiment, however, the fabric structure can be a combination of conductive yarns and non-conductive yarns. When combining conductive yarns and non-conductive yarns, a fabric can be produced that has the feel, drape characteristics, and other properties of typical fabrics used to produce garments and the like. Thus, the electrically conductive yarns can be incorporated into the fabric without undesirably increasing stiffness or imparting any other undesirable characteristics into the fabric.

In general, conductive yarns for use in fabrics of the present disclosure can be made from any suitable conductive material. The conductive material, for instance, may comprise a metal, a metallic compound, a conductive polymer, or mixtures thereof. The yarn can comprise a monofilament yarn, a multifilament yarn, and possibly a spun yarn. In one embodiment, for instance, the conductive yarns comprise monofilament yarns. The entire yarn can be made from a conductive material. Alternatively, the yarn may comprise a multicomponent yarn containing a conductive component and a non-conductive component. For instance, in one embodiment, the multicomponent yarn may comprise a bicomponent yarn in which the conductive component comprises the core surrounded by a non-conductive sheath. Alternatively, the conductive component may comprise the sheath while the non-conductive component may comprise the core. In still another embodiment, the conductive component and the non-conductive component can be in a side-by-side relationship within the yarn.

In one embodiment, the conductive yarn comprises a core-sheath type conductive fiber, such as a monofilament fiber containing a core made from a conductive polymer. For instance, the conductive polymer used to make the core may comprise an acetylene conductive polymer, a pyrrole conductive polymer, a thiophene-based conductive polymer, a phenylene conductive polymer, an aniline conductive polymer, or the like.

For example, the conductive portion of the fiber may comprise an acetylene-based, 5-membered heterocyclic system. Monomers that may be used to produce the conductive polymer include, for instance, 3-methylpyrrole, 3-ethylpyrrole, 3-dodecylpyrrole 3-alkylpyrrole, 3,4-dimethylpyrrole, 3-methyl-4-3,4-dialkylpyrrole, dodecylpyrrole, N-methylpyrrole, N-alkylpyrrole such as N-dodecylpyrrole, N-methyl-3-methylpyrrole, N-alkyl-3-alkylpyrrole such as N-ethyl-3-dodecylpyrrole, 3-carboxymethylpyrrole, and the like. In an alternative embodiment, the conductive polymer may comprise a thiophene-based polymer such as an isothianaphthene-based polymer. Other examples of thiophene-based conductive polymers include poly-3,4-ethylene dioxythiophene. An example of a phenylene conductive polymer is poly-p-phenylene vinylene. The above polymers can also be mixed together in forming the conductive portion of a yarn.

In one embodiment, a dopant may be added to the conductive polymer in order to improve conductivity. The dopant, for instance, may comprise a halide ion, such as a chloride ion, or a bromide ion. Other dopants include perchlorate ions, tetrafluoroborate ions, hexafluoroarsenate ions, sulfate ions, nitrate ions, thiocyanate ions, hexafluoride silicic acid ions, trifluoroacetate ions, phosphate ions, phenylphosphate ions, and the like. Particular examples of dopants include hexafluorophosphate ions, tosylate ions, ethylbenzene sulfonate ions, alkylbenzene sulfonate ions such as dodecylbenzene sulfonate ions, methylsulfonate ions, other alkyl sulfonate ions, polyacrylic acid ions, polyvinyl sulfonic acid ions, polystyrene sulfonate ions, poly(2-acrylamido-2-methylpropanesulfonic acid ions, and the like. The amount of dopant added to the conductive polymer can vary depending upon the particular application. For instance, the dopant can be combined with the conductive polymer in an amount from about 3% to about 50% by weight, such as from about 10% to about 30% by weight.

In one embodiment, a conductive portion of a multicomponent fiber can be formed by applying a metallic coating to a polymer resin. The polymer resin can comprise any of the conductive polymers described above or can comprise a non-conductive polymer. In an alternative embodiment, a conductive filler can be loaded into a thermoplastic resin. The thermoplastic resin can comprise a conductive polymer as described above or non-conductive polymer.

Metals well suited for coating a polymer material include gold, silver, chrome, iron, and the like. Conductive particles that may be used include any of the metals described above in addition to aluminum, graphite, other carbon particles, carbon fibers, carbon black, and the like.

In yet another embodiment, the conductive portion of the multicomponent fiber or filament may comprise a carbon filament.

In one particular embodiment, the electrically conductive composite fiber of the present disclosure includes a conductive polymer layer made of a thermoplastic polyamide containing from about 13% to about 60% by weight of an electrically conductive particulate matter, such as carbon black, graphite, boron nitride, or the like. The fiber further includes a non-conductive component made of a thermoplastic polyamide.

In another embodiment, the conductive yarn comprises a thermoplastic polymer covered with a metal, such as silver or stainless steel. The thermoplastic polymer may comprise, for instance, a polyamide such as nylon or a polyester.

Multicomponent fibers and yarns made in accordance with the present disclosure can include a non-conductive component in addition to a conductive component. The non-conductive component can be made from any suitable natural or synthetic polymer. For instance, the non-conductive portion can be made from a polyamide, such as nylon 6 or nylon 66. Alternatively, the non-conductive portion can comprise a polyester, such as polyethylene terephthalate, polybutylene terephthalate, copolymers thereof, and the like. In yet another embodiment, the non-conductive component may comprise a polyolefin, such as polyethylene or polypropylene including copolymers thereof. In yet another embodiment, the non-conductive portion may comprise a polyacrylonitrile or a polyvinyl alcohol polymer. The relative amounts of the conductive component in relation to the non-conductive component can vary widely depending upon various different factors. The amount of the conductive component, for instance, can depend on the conductivity of the material and the type of materials being used. In general, the conductive component can comprise from about 20% to about 90% of the multicomponent fiber, such as from about 30% to about 70% by weight.

In another embodiment of the present disclosure, the conductive yarn may comprise a multifilament yarn containing conductive filaments. For instance, a multifilament yarn can be formed in which one or more conductive filaments can be surrounded by non-conductive filaments. The non-conductive filaments can be made from any of the non-conductive thermoplastic polymers described above. The conductive filaments, on the other hand, can be made from any of the conductive materials described above including conductive polymers, a metallic material, and the like.

In yet another embodiment, a multifilament yarn made from thermoplastic filaments can be covered with carbon nanotube to render the yarn conductive.

The conductive yarns made in accordance with the present disclosure can be woven or knitted into any suitable fabric structure capable of carrying out the process of the present disclosure. As described above, the fabric structure can be made entirely from conductive yarns. Alternatively, the fabric can be made from a combination of conductive yarns and non-conductive yarns. For instance, the conductive yarns can be strategically placed within the fabric in order to form a countless variety of different electrical circuits for use in carrying out the processes of the present disclosure.

In one embodiment, the fabric structure of the present disclosure comprises a knitted fabric containing conductive yarns and non-conductive yarns. In general, any suitable knitting machine may be used in accordance with the present disclosure. For instance, the knitting machine may comprise a weft knitting machine, a warp knitting machine, or a seamless knitting machine. In one embodiment, for instance, a Santoni circular knitting machine is used. Knitting machines for use in the present disclosure offer various advantages and benefits. For instance, through the use of a knitting machine, a three-dimensional knitted architecture can be constructed that can advantageously place conductive yarns in needed locations. In addition, many knitting machines allow users to select needle-to-needle operations electronically and can have a variety of different yarn feeders.

In one embodiment, for instance, the fabric is formed or knitted on a circular knitting machine that has a computerized electronic needle and yarn feed selection system. Typically cylindrical blanks are knitted using both the cylindrical needles and the dial needles. The cylinder needles knit a first series of courses and the dial needles can knit a second series of courses.

Alternatively, the knitting machine can include more than two courses. For instance, the knitting machine can include from about two to about sixteen courses, such as from about six to about twelve courses.

In one embodiment, a knitting machine can be used with eight feeders. A fabric can be made having a three-dimensional configuration from the knitting machine. For instance, a double-faced fabric can be produced. In this manner, the face of the fabric can include primarily only non-conductive yarns, while the back of the fabric can include conductive yarns. For instance, a plating technique can be used to produce the fabric. Plating is a knit construction in which two or more yarns are fed simultaneously. The second yarn is generally of a different type than the first yarn. During the knitting process, the second yarn is placed under the first yarn so that each yarn can be rolled to a specific side of the fabric. In this manner, one yarn can appear primarily on the face of the fabric and the other yarn can primarily appear on the back of the fabric.

In one embodiment, in addition to a non-conductive yarn and a conductive yarn, the fabric can include various other yarns. For instance, the fabric can include an elastic yarn that when stretched recovers. For instance, the elastic yarn may comprise Spandex.

In one embodiment, for instance, the knitted yarn may be formed from about four to about six courses. The first course, for instance, can be made from a non-conductive yarn, such as polyester, cotton, nylon, an acrylic polymer, or the like. The remaining courses, on the other hand, can comprise a single yarn or a combination of yarns. For instance, one of the courses can contain a conductive yarn in conjunction with a spandex yarn. A third course, on the other hand, may contain a non-conductive yarn in combination with a spandex yarn. A fourth course, on the other hand, may be made exclusively from the conductive yarn. All different combinations can be used and all different numbers of courses can be used to form the fabric. In this manner, a three-dimensional fabric architecture can be constructed particularly well suited for constructing electric circuits within the fabric and for the fabric to carry out the commands that are user inputted. During knitting, float loops can be used in order to obtain the desired construction.

Referring again to FIG. 1, the sensor data obtained by the sensor devices 106 can be provided to the computing device 104. The computing device 104 can include a corporeal data determiner 108 and an ergonomic assessor 110. The corporeal data determiner 108 can be configured to extract posture and/or motion data from the sensor data provided by the sensor devices 106. For instance, the raw sensor data obtained by the computing device 104 can be analyzed by the corporeal data determiner 108 to identify, determine, and/or extract features indicative of corporeal data. More particularly, various attributes, characteristics, or patterns of the sensor data can be determined to correspond to various motions, postures, bend angles, etc. of the user. The corporeal data determiner 108 can analyze the data obtained by the sensor devices 106 to identify features indicative of such attributes, characteristics, or patterns. In this manner, various portions of the sensor data may possess such attributes, characteristics, or patterns. Such portions of the sensor data can be classified by the corporeal data determiner 108 as various types of corporeal data.

Such corporeal data can be associated with a bend angle of at least one body segment of the user. For instance, the corporeal data can include a shoulder angle (e.g. relative to the side of the user's body), a back angle (e.g. front to back angle), torso angle (e.g. side to side angle). In some implementations, the corporeal data can be associated with a shoulder rotation (e.g. about the socket joint) of the user. In some implementations, the corporeal data can further include a speed and/or acceleration with which motion by a user is performed, a duration of motion associated with the user, and/or a repetitive nature of motion. It will be appreciated that the corporeal data can include data associated with various other suitable movements, postures, body segments, etc. In some implementations, the corporeal data can include behavior data. The behavior data can be indicative of a job activity performed, productivity estimates (e.g., number of towels folded per minute).

Figure 2:
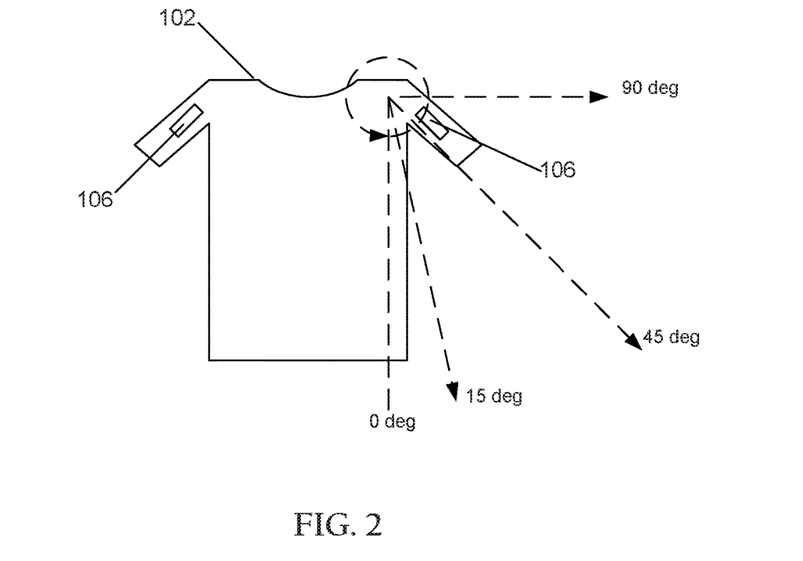
FIG. 2 depicts an example ergonomic assessment garment according to example aspects of the present disclosure.

FIG. 2 depicts an example bend angle associated with a shoulder of the user. As indicated, the corporeal data can include a shoulder angle relative to the side of the body. As shown in FIG. 2, a sensor device 106 can be positioned with respect to the shoulder of a user such that the sensor device 106 can obtain sensor data indicative of the shoulder angle. In this manner, the shoulder angle can be determined based at least in part on the sensor data obtained by the sensor device 106. As shown, the shoulder angle can be any suitable angle (e.g. 15 degrees, 45 degrees, 90 degrees, etc.) relative to the side of the user's body while wearing the ergonomic assessment garment 102. Measurements can be taken within a full 360 degree range across multiple planes. The sensor devices 106 and/or other sensor devices positioned elsewhere with respect to the ergonomic assessment garment 102 can further be configured to obtain sensor data indicative of a posture and/or motion of various other suitable body segment of the user while wearing the ergonomic assessment garment 102.

The corporeal data determined by the corporeal data determiner 108 can be used by the ergonomic assessor 110 to determine an ergonomic assessment associated with the posture and/or motion of the user. The ergonomic assessment can include any suitable information associated with the posture and/or motion of the user. More particularly, the ergonomic assessment can include one or more determinations as to the quality and/or safety of the motion and/or posture of one or more body segments of the user. Such determinations can correspond to a categorization of the user's motion and/or posture into one or more ergonomic zones. An ergonomic zone can be determined for a body segment based at least in part on the motion and/or posture (e.g. bend angle(s)) of the body segment during one or more measurement periods. A measurement period can be any suitable period of time during which data is being collected to facilitate an assessment of the user's motion and/or posture. In some implementations, the measurement period can be initiated by a user, for instance, via interaction with the ergonomic assessment garment 102, the computing device 104 or other suitable computing device.

In some implementations, the ergonomic zones in which the user and/or the user's motion can be classified can be defined based at least in part on a number of instances in which the bend angle of the subject body segment exceeded a threshold during one or more measurement periods. For instance, the ergonomic zone can be defined based at least in part on an average number of instances in which the bend angle of the subject body segment exceeded the threshold during each of a plurality of subset periods of the one or more measurement periods. In some implementations, the ergonomic zones can be defined based at least in part on an amount of time (e.g. an average amount of time) during which the bend angle of the subject body segment exceeded the threshold during the one or more measurement periods. Such amount of time can be quantified as a ratio of time in which the threshold is exceeded to total time of the one or more measurement periods. The ergonomic zones can be defined to indicate various tiers of posture and/or motion acceptability. For instance, a first ergonomic zone can indicate an acceptable motion and/or posture, a second ergonomic zone can indicate a less acceptable motion and/or posture, and a third ergonomic zone can indicate an even less acceptable motion and/or posture.

The ergonomic zones can be defined such that the motion and/or posture of the user and/or the subject body segment will be categorized in a particular ergonomic zone based at least in part on a number of instances and/or an amount of time in which the bend angle of the subject body segment exceeds the threshold. In this manner, the number of instances and/or amount of time in which the body segment exceeds the threshold during the one or more measurement periods can be corresponded to a level of quality, safety, and/or acceptability of the motion and/or posture of the body segments via classification in an ergonomic zone.

As indicated, each subject body segment for which data is being collected can be categorized within a respective ergonomic zone corresponding to the subject body segment. In some implementations, the ergonomic assessor 110 can further determine an overall ergonomic zone for the user. The overall ergonomic zone can be determined based at least in part on the ergonomic zones determined for each subject body segment. In this manner, the overall ergonomic zone can indicate an overall quality, safety, and/or acceptability of the motion and/or posture of the user. In some implementations, the overall ergonomic zone can correspond to the most severe ergonomic zone (e.g. ergonomic zone corresponding to the least acceptable posture and/or motion) in which a subject body segment of the user has been classified. In some implementations, the overall ergonomic zone can correspond to an aggregation of each ergonomic zone associated with each subject body segment.

The ergonomic assessment can further include one or more power expenditure metrics associated with the user. A power expenditure metric can be determined for a subject body segment, and can be an estimation of an amount of power expended by the subject body segment during the one or more measurement periods. The power expenditure metric can be determined based at least in part on a speed and/or acceleration of the motion of the subject body segment. More particularly, the power expenditure metric can be determined based at least in part on an angular velocity and/or an angular acceleration of the motion of the body segment. In some implementations, the power expenditure metric can be relative to a maximum acceptable power value for the user. The ergonomic assessor 110 can further aggregate the power expenditure metrics for each subject body segment to determine an overall power expenditure by the user.

The ergonomic assessment can further include a productivity assessment associated with the user. The productivity assessment can include information indicative of time periods when the user was active, time periods when the user was resting, a number of rests taken by the user, a duration of the rests, an average duration of the rests, duration between rests, total time of the measurement period, type of activities being performed, an estimated quantity of output per unit time for certain job functions, and/or other suitable productivity measures. The type of activities being performed can include a description of the performed activities. For instance, the ergonomic assessor 110 can determine such type of activity based at least in part on the sensor data and/or the corporeal data. For instance, such description can specify tasks, such as "folding items," "stacking items," "transferring items from a first surface to a second surface," "loading or unloading cargo," etc. In some implementations, the productivity assessment can be based at least in part on behavior data included in the corporeal data.

The ergonomic assessor 110 can provide the ergonomic assessment for display, for instance, on the computing device 104 or other suitable computing device. The ergonomic assessment can be displayed within a user interface, such that the user can view the relevant information provided by the ergonomic assessment.

The ergonomic assessment can be used to provide haptic feedback to the user. For instance, the ergonomic assessment garment 102 can include one or more feedback devices, such as vibration motors, actuators, etc. implemented with or otherwise attached to the ergonomic assessment garment 102. Such feedback devices can be configured to provide haptic feedback to the user based at least in part on the ergonomic assessment. For instance, the computing device 104 can be configured to determine one or more haptic feedback signals based at least in part on the ergonomic assessment, corporeal data and/or sensor data, and to provide such haptic feedback signals to the user via the feedback devices. In some implementations, the feedback signals can include vibration patterns associated with one or more ergonomic zones, a power expenditure metrics, etc. determined for the user. For instance, vibration having a first vibratory pattern can be provided to the user to indicate that the motion and/or posture of the user is classified as within a first ergonomic zone. Vibration having a second pattern can be provided to the user to indicate that the motion and/or posture of the user is classified as within a second ergonomic zone.

In some implementations, the ergonomic assessment garment 102 can be calibrated based on the user wearing the ergonomic assessment garment 102. For instance, the calibration can be performed by the computing device 104 based at least in part on sensor data from the sensor devices 106. Such calibration can indicate one or more reference points from which the ergonomic assessment can be determined. The reference points can be indicative, for instance, of a natural posture of the user. In this manner, the calibration can be performed prior to the determination of the ergonomic assessment by the ergonomic assessor 110.

Figure 3:
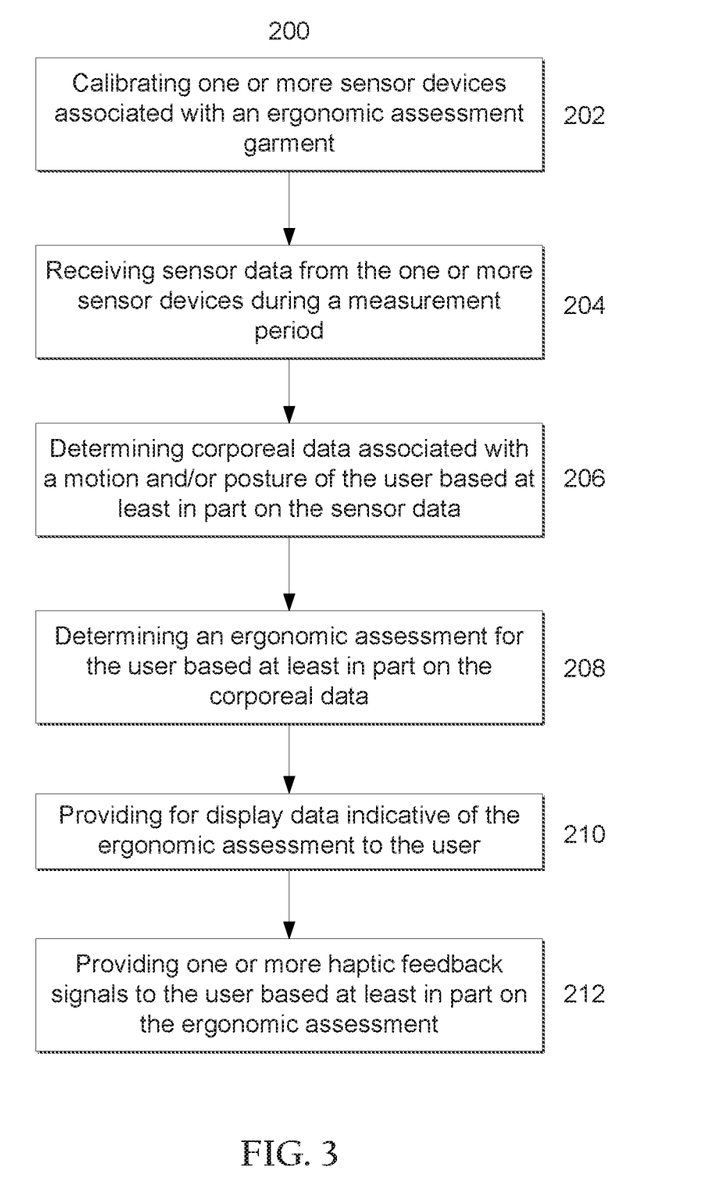
FIG. 3 depicts a flow diagram of an example method of determining an ergonomic assessment according to example aspects of the present disclosure.

FIG. 3 depicts a flow diagram of an example method (200) of determining an ergonomic assessment according to example aspects of the present disclosure. Method (200) can be implemented by one or more computing devices, such as one or more of the computing devices depicted in FIG. 4. In particular implementations, the method (200) can be implemented by corporeal data determiner 108 and/or the ergonomic assessor 110 of FIG. 1. In addition, FIG. 3 depicts steps performed in a particular order for purposes of illustration and discussion. Those of ordinary skill in the art, using the disclosures provided herein, will understand that the steps of any of the methods discussed herein can be adapted, rearranged, expanded, omitted, or modified in various ways without deviating from the scope of the present disclosure.

At (202), the method (200) can include calibrating one or more sensor devices associated with an ergonomic assessment garment. As indicated the ergonomic assessment garment can be any suitable garment configured to obtain data indicative of a user's motion and/or posture. In some implementations, the ergonomic assessment garment can be a smart garment constructed using one or more electrically conductive yarns. The electrically conductive yarns can be configured to form one or more circuits to facilitate example aspects of the present disclosure. The ergonomic assessment garment can include one or more sensor devices (e.g. accelerometers, gyroscopes, inertial measurement units, etc.) configured to obtain data indicative of the user's motion and/or posture. In implementations wherein the ergonomic assessment garment is a smart garment, the sensor device(s) can be coupled to one or more electrically conductive yarns.

The sensor devices of the ergonomic assessment garment can be calibrated to a user wearing the ergonomic assessment garment. The calibration can provide a baseline or reference for measuring the motion and/or posture of the user. The calibration can indicate a natural posture of the user from which the motion and/or posture changes can be measured.

At (204), the method (200) can include receiving sensor data from the one or more sensor devices during a measurement period. As indicated, a measurement period can be any suitable period of time during which data is obtained by the sensor devices to facilitate a determination of an ergonomic assessment for the user. The sensor data can include raw sensor data indicative of the motion and/or posture of the user during the measurement period.

At (206), the method (200) can include determining corporeal data associated with the motion and/or posture of the user based at least in part on the sensor data. For instance, determining the corporeal data can include identifying and/or extracting various features from the raw sensor data indicative of various motions, bend angles, speeds, accelerations, etc. of the user during the measurement period. The features can correspond to various attributes, characteristics, or patterns of the sensor data. In this manner, the features can be extracted at various times from various portions of the sensor data to identify various motions, bend angles, etc. of the user performed by the user.

At (208), the method (200) can include determining an ergonomic assessment for the user based at least in part on the corporeal data. The ergonomic assessment can include suitable information relating to the posture and/or motion of the user during the measurement period. For instance, the ergonomic assessment can indicate a classification of one or more subject body segments of the user within ergonomic zones indicating the acceptability, quality and/or safety of the user's motion and/or posture during the measurement period. The ergonomic zones for a subject body segment can be defined based at least in part on a number of instances in which a bend angle of the subject body segment exceeded a threshold during the measurement period. In some implementations, the ergonomic zones for a subject body segment can be defined based at least in part on a ratio of time in which the bend angle exceeded the threshold to total time of the measurement period. In some implementations, an overall ergonomic zone can be determined for the user corresponding to the most severe ergonomic zone (e.g. corresponding to the least acceptable posture and/or motion) determined for a subject body segment during the measurement period.

The ergonomic assessment can further include power expenditure metrics for one or more subject body segments. The power expenditure metrics can be determined based at least in part on a speed and/or acceleration of motion of the subject body segment. In some implementations, an overall power expenditure metric can be determined corresponding to an aggregation of each power expenditure metric for each subject body segment. In some implementations, the ergonomic assessment can include a productivity assessment. The productivity assessment can indicate monitored periods of work, periods of rest, number of rests (e.g. average number of rests), duration of rests (e.g. average duration of rests), types of work being performed, an estimated quantity of output per unit time for certain job functions, and/or any other suitable productivity measures. Such productivity assessment can be determined from the sensor data and/or the corporeal data.

By way of example, the ergonomic assessment can be associated with an assessment of the user associated with one or more activities. The activities can include, for example, one or more of a medical rehabilitation, a sports performance, and an evaluation of an injury (e.g., tracking and injury prevention). For instance, information such the bend angle, achieved ergonomic zones, power expenditure metric, etc. can be analyzed to indicate how a user is progressing during medical rehabilitation (e.g., whether the user's range of motion, power is increasing), whether the user is maximizing a range of motion for peak sports performance (e.g., on a javelin throw), and/or whether the body segment is moving into a zone that may be indicative of an increased risk of injury (e.g., hyperextension).

At (210), the method (200) can include providing data indicative of the ergonomic assessment to a user interface of a computing device associated with the user. For instance, the data indicative of the ergonomic assessment can be provided for display in a graphical user interface of the computing device. In this manner, the user can be informed of the ergonomic assessment, such that the user can receive the opportunity to adjust the user's posture and/or motion. For instance, the user can be informed as to how the user is performing with respect to a medical rehabilitation, sports performance, injury evaluation, etc.

At (212), the method (200) can include providing haptic feedback signals to the user based at least in part on the ergonomic assessment. The ergonomic assessment garment can include one or more haptic feedback devices. Such haptic feedback devices can, for instance, be coupled to one or more electrically conductive yarns of the ergonomic assessment garment. The haptic feedback signals can be determined based at least in part on the ergonomic assessment, corporeal data, and/or sensor data, and provided to the user via the feedback devices.

Figure 4:
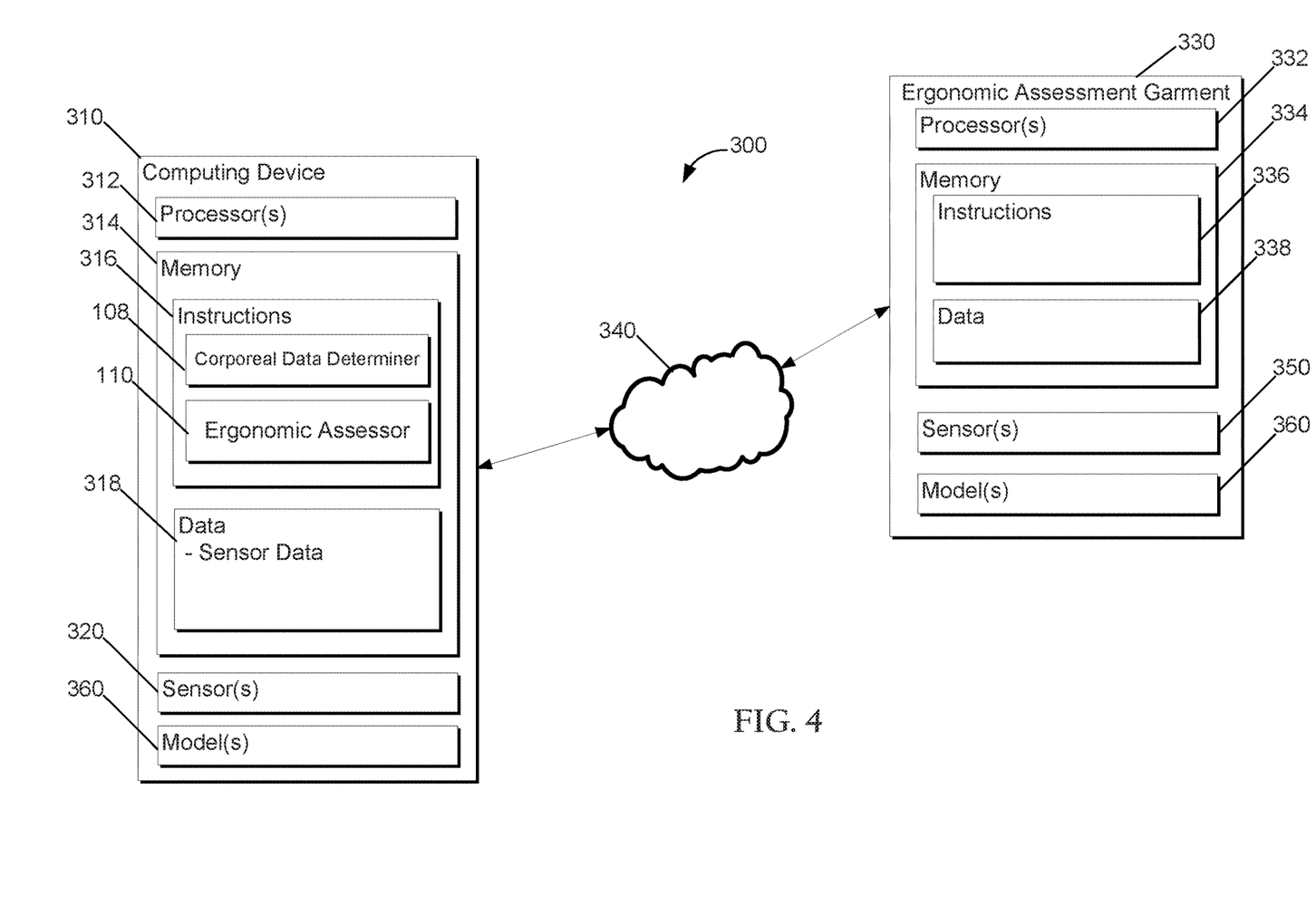
FIG. 4 depicts an example system according to example aspects of the present disclosure.

FIG. 4 depicts an example computing system 300 that can be used to implement the methods and systems according to example aspects of the present disclosure. The system 300 can be implemented using a client-server architecture that includes a computing device 310 that communicates with one or more ergonomic assessment garments 330 over a network 340. The system 300 can be implemented using other suitable architectures, such as a single computing device.

The system 300 includes a computing device 310. The computing device 310 can be any suitable type of computing device, such as a general purpose computer, special purpose computer, laptop, desktop, mobile device, navigation system, smartphone, tablet, wearable computing device, a display with one or more processors, or other suitable computing device. In some implementations, the computing device 310 can be integrated or implemented within an ergonomic assessment garment 330. In some implementations, the computing device 310 can be a separate and distinct device from the ergonomic assessment garment 330, and can be located at a remote location from the ergonomic assessment garment 330. In some implementations, the computing device can include one or more sensor devices 320. For instance, the sensor devices can include one or more accelerometers, gyroscopes, inertial measurement units, force gauges, tachometers, electromyography sensors, heart rate monitors, and/or other suitable sensors. The sensor devices 320 may be contained within or otherwise physically connected to the computing device 310. In this manner, the computing device 310 and the sensors 320 can be attached, affixed, or otherwise connected to the ergonomic assessment garment 330 to obtain sensor data indicative of the motion and/or posture of a user wearing the ergonomic assessment garment 320.

The computing device 310 can include one or more processors 312 and one or more memory devices 314. The computing device 310 can also include a network interface used to communicate with the ergonomic assessment garment 330 and/or other suitable computing devices, such as a server computing device, for instance, over the network 340. The network interface can include any suitable components for interfacing with one more networks, including for example, transmitters, receivers, ports, controllers, antennas, or other suitable components.

The one or more processors 312 can include any suitable processing device, such as a microprocessor, microcontroller, integrated circuit, logic device, or other suitable processing device. The one or more memory devices 314 can include one or more computer-readable media, including, but not limited to, non-transitory computer-readable media, RAM, ROM, hard drives, flash drives, or other memory devices. The one or more memory devices 314 can store information accessible by the one or more processors 312, including computer-readable instructions 316 that can be executed by the one or more processors 312. The instructions 316 can be any set of instructions that when executed by the one or more processors 312, cause the one or more processors 312 to perform operations. For instance, the instructions 316 can be executed by the one or more processors 312 to implement the corporeal data determiner 108 and the ergonomic assessor 110 described with reference to FIG. 1.

As shown in FIG. 4, the one or more memory devices 314 can also store data 318 that can be retrieved, manipulated, created, or stored by the one or more processors 312. The data 318 can include, for instance, sensor data and other data. The data 318 can be stored locally at the computing device 310 and/or in one or more databases. The one or more databases can be connected to the computing device 310 by a high bandwidth LAN or WAN, or can also be connected to computing device 310 through network 340. The one or more databases can be split up so that they are located in multiple locales.

The computing device 310 can exchange data with one or more ergonomic assessment garments 330, or other suitable computing devices over the network 340. Although one ergonomic assessment garment 330 is illustrated in FIG. 4, any number of ergonomic assessment garments 330 can be connected to the computing device 310 over the network 340. The ergonomic assessment garment 330 can be any suitable garment. In some implementations, the ergonomic assessment garment can be a smart garment constructed using one or more electrically conductive yarns configured to form one or more circuits to implement example aspects of the present disclosure. In some implementations, the ergonomic assessment garment can include one or more sensor devices 350. For instance, such implementations can include implementations wherein the computing device 310 is located remotely from the ergonomic assessment garment.

In some implementations, the computing device 310 can be communicatively coupled to one or more additional computing devices. For instance, the computing device 310 may be configured to provide data indicative of an ergonomic assessment to such one or more additional computing devices, for instance, for display of the ergonomic assessment to the user by display device(s) associated with the one or more additional computing devices. In some implementations, the one or more additional computing devices can include a server computing device configured to, with user consent, obtain a plurality of ergonomic assessments from a plurality of ergonomic assessment garments and/or associated computing devices. As indicated, such server computing device can then be configured to aggregate and analyze such ergonomic assessments to determine trends, patterns, etc. associated with the ergonomic assessments. In some implementations, such a server computing device can communicate with one or more ergonomic assessment garments 330 (e.g., via a companion application, direct communication) to facilitate the functions of the ergonomic assessment garments 330. For example, the server computing device (e.g., a companion application to an application of the garment) can communicate with one or more ergonomic assessment garments 330 to cause and/or facilitate one or more functions of the respective ergonomic assessment garment 330 (e.g., gathering sensor data, processing sensor data, determining corporeal data, determining an ergonomic assessment, etc.). For example, the server computing device can provide/update the data analytical tools of the ergonomic assessment garment 330 over time.

In some implementations, the computing device 310 can host (or otherwise be associated with) a cloud-based service that provides ergonomic assessments. For instance, the computing device 310 can be associated with a service that acquires data associated with one or more ergonomic assessment garments 330, such as data indicative of the individual ergonomic assessments. The computing device 310 (e.g., remote from the ergonomic assessment garments) can aggregate the data from the one or more ergonomic assessment garments 330 (e.g., that can be associated with the same or different individuals) over time. The computing device 310 can determine an aggregate ergonomic assessment and/or an ergonomic assessment trend based on such data. The aggregate ergonomic assessment and/or trend can be provided to individuals, enterprise customers of the cloud-based service, etc. for medical-related tracking, sports related tracking, injury prevention, and/or other purposes.

In some implementations, the ergonomic assessment garment 330 and/or the computing device 310 can store or include one or more models 360. For example, the models 360 can be or can otherwise include various machine-learned models such as neural networks (e.g., deep neural networks) or other multi-layer non-linear models. Neural networks can include recurrent neural networks (e.g., long short-term memory recurrent neural networks), feed-forward neural networks, or other forms of neural networks.

In some implementations, the ergonomic assessment garment 330 and/or the computing device 310 can receive the one or more models 360 over network 340 (e.g., from another computing device), store the one or more models 360 in the memory 314/334, and use or otherwise implement the one or more models 360 by the one or more processors 312/332. In some implementations, the ergonomic assessment garment 330 and/or the computing device 310 can implement multiple parallel instances of a single model 360 (e.g., to perform parallel garment calibrations and/or trend analysis).

The model 360 can be trained to calibrate the ergonomic assessment garment 330 and/or to determine ergonomic assessment trends. For instance, the model 360 can receive an input including, at least, corporeal data, sensor data, and/or other data associated with the user. The model 360 can be trained to provide a model output that is indicative of an ergonomic assessment associated with the user. The model output can be based at least in part on the model input (e.g., corporeal data). Additionally, or alternatively, the model 360 can be trained to determine an aggregate ergonomic assessment and/or one or more ergonomic assessment trends. For instance, the model 360 can receive an input including a plurality of ergonomic assessments (e.g., from an individual user, multiple users). The model 360 can be trained to provide a model output that is indicative of a trend in the ergonomic assessments (e.g., assessment patterns over time, repetitive characteristics, other trends). The model output can be based at least in part on the model input (e.g., the plurality of ergonomic assessments).

Additionally or alternatively, one or more models 360 can be included in or otherwise stored and implemented by a server computing system (e.g., remote from the computing device 310 and/or the ergonomic assessment garment 330) that communicates with the computing device 310 and/or the ergonomic assessment garment 330 according to a client-server relationship. For example, the models 360 can be implemented by the server computing system as a portion of a web service. Thus, one or more models 360 can be stored and implemented at the computing device 310 and/or the ergonomic assessment garment 330 and/or one or more models 360 can be stored and implemented at the server computing system.

The models 360 can be trained via interaction with a training computing system that is communicatively coupled over the network 340. The training computing system can be separate from the server computing system, the computing device 310 and/or the ergonomic assessment garment 330 or can be a portion of the server computing system, the computing device 310 and/or the ergonomic assessment garment 330.

The training computing system can include a model trainer that trains the machine-learned models 360 using various training or learning techniques, such as, for example, backwards propagation of errors. In some implementations, performing backwards propagation of errors can include performing truncated backpropagation through time. The model trainer can perform a number of generalization techniques (e.g., weight decays, dropouts, etc.) to improve the generalization capability of the models being trained. In some implementations, supervised training techniques can be used on a set of labeled training data.

In particular, the model trainer can train a model 360 based on a set of training data. The training data can include, for example, a number of previous ergonomic assessments and/or corporeal data (and/or sensor data) associated therewith. In some implementations, the training data can include labeled ergonomic assessment data. The training data can be labeled manually, automatically or using a combination of automatic labeling and manual labeling.

In some implementations, if the user has provided consent, the training examples can be provided by the ergonomic assessment garment 330. Thus, in such implementations, the model 320 can be trained by the training computing system on user-specific communication data received from the ergonomic assessment garment 330. In some instances, this process can be referred to as personalizing the model.

In implementations wherein the computing device 310 is a separate and distinct device located remotely from the ergonomic assessment garment 330, the ergonomic assessment garment 330 can include one or more processor(s) 332 and a memory 334. For instance, such processors(s) 332 and/or memory 334 can be used to obtain sensor data from the sensor devices 350, and to provide the sensor data to the computing device 310, for instance, via the network 340. The one or more processor(s) 332 can include one or more central processing units (CPUs), and/or other processing devices. The memory 334 can include one or more computer-readable media and can store information accessible by the one or more processors 332, including instructions 336 that can be executed by the one or more processors 332 and data 338.

The ergonomic assessment garment 330 and/or the computing device 310 of FIG. 4 can include various input/output devices for providing and receiving information from a user, such as a mechanism or other means of initiating and ceasing a measurement period. In some implementations, the computing device 310 can include a display device for presenting a user interface for displaying ergonomic assessments according to example aspects of the present disclosure.

The ergonomic assessment garment 330 can also include a network interface used to communicate with one or more remote computing devices (e.g. computing device 310) over the network 340. The network interface can include any suitable components for interfacing with one more networks, including for example, transmitters, receivers, ports, controllers, antennas, or other suitable components.

The network 340 can be any type of communications network, such as a local area network (e.g. intranet), wide area network (e.g. Internet), cellular network, or some combination thereof. The network 340 can also include a direct connection between a ergonomic assessment garment 330 and the computing device 310. In general, communication between the computing device 310 and a ergonomic assessment garment 330 can be carried via network interface using any type of wired and/or wireless connection, using a variety of communication protocols (e.g. TCP/IP, HTTP, SMTP, FTP), encodings or formats (e.g. HTML, XML), and/or protection schemes (e.g. VPN, secure HTTP, SSL).

The technology discussed herein makes reference to servers, databases, software applications, and other computer-based systems, as well as actions taken and information sent to and from such systems. One of ordinary skill in the art will recognize that the inherent flexibility of computer-based systems allows for a great variety of possible configurations, combinations, and divisions of tasks and functionality between and among components. For instance, server processes discussed herein may be implemented using a single server or multiple servers working in combination. Databases and applications may be implemented on a single system or distributed across multiple systems. Distributed components may operate sequentially or in parallel.

While the present subject matter has been described in detail with respect to specific example embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A system for determining an ergonomic assessment associated with a user, comprising:
    an ergonomic assessment garment;
    one or more sensors implemented with the ergonomic assessment garment; and
    one or more processors implemented with the ergonomic assessment garment and configured to:
        receive sensor data associated with the one or more sensors during a measurement period;
        determine corporeal data associated with at least one body segment of the user based at least in part on the sensor data, the corporeal data associated with at least one of a velocity, an acceleration, or a bend angle associated with the at least one body segment;
        determine one or more ergonomic zones based at least in part on the measurement period and the at least one of the velocity, the acceleration, or the bend angle associated with the at least one body segment during the measurement period, wherein the one or more ergonomic zones are based at least in part on a number of instances in which the at least one of the velocity, the acceleration, or the bend angle associated with the at least one body segment exceeds one or more thresholds during the measurement period; and
        determine the ergonomic assessment associated with the user based at least in part on the corporeal data, the ergonomic assessment comprising an indication of one or more ergonomic zones associated with the user.

2. The system of claim 1, wherein the corporeal data comprises data associated with a timing of the at least one of the velocity, the acceleration, or the bend angle of the at least one body segment relative to the one or more thresholds.

3. The system of claim 2, wherein determining corporeal data for at least one body segment of the user comprises measuring an amount of time that the at least one of the velocity, the acceleration, or the bend angle of the at least one body segment is greater than the one or more thresholds.

4. The system of claim 3, wherein determining the one or more ergonomic zones associated with the user comprises determining the one or more ergonomic zones based at least in part on the amount of time that the at least one of the velocity, the acceleration, or the bend angle of the at least one body segment is greater than the one or more thresholds.

5. The system of claim 1, wherein determining the ergonomic assessment associated with the user comprises determining an assessment of an expenditure of power by the user.

6. The system of claim 1, further comprising providing one or more haptic feedback signals to the user via the ergonomic assessment garment based at least in part on the ergonomic assessment.

7. The system of claim 1, wherein the ergonomic assessment garment is a smart garment constructed at least in part using electrically conductive yarns woven into a fabric structure of the ergonomic assessment garment.

8. The system of claim 1, wherein the one or more sensors comprise one or more accelerometers implemented within the ergonomic assessment garment to facilitate a measurement of a motion or posture associated with the at least one body segment.

9. The system of claim 1, wherein the corporeal data additionally comprises data associated with a range of motion of the at least one body segment.

10. A computing system, comprising:
    one or more processors; and
    one or more memory devices, the one or more memory devices storing computer-readable instructions that when executed by the one or more processors cause the one or more processors to perform operations, the operations comprising:
        receiving, by one or more computing devices, sensor data from one or more sensors during a measurement period, the one or more sensors implemented with an ergonomic assessment garment worn by a user;
        determining, by the one or more computing devices, corporeal data associated with at least one body segment of the user based at least in part on the sensor data, the corporeal data associated with at least one of a velocity, an acceleration, or a bend angle associated with the at least one body segment;
        determining, by the one or more computing devices, one or more ergonomic zones based at least in part on the measurement period and the at least one of the velocity, the acceleration, or the bend angle associated with the at least one body segment during the measurement period, wherein the one or more ergonomic zones are based at least in part on an amount of time during which the at least one of the velocity, the acceleration, or the bend angle associated with the at least one body segment exceeds one or more thresholds during the measurement period; and
        determining, by the one or more computing devices, an ergonomic assessment associated with the user based at least in part on the corporeal data, the ergonomic assessment comprising an indication of one or more ergonomic zones associated with the user.

11. The computing system of claim 10, wherein the corporeal data comprises data associated with a timing of the at least one of the velocity, the acceleration, or the bend angle of the at least one body segment relative to the one or more thresholds.

12. The computing system of claim 11, wherein determining corporeal data for at least one body segment of the user comprises measuring the amount of time that the at least one of the velocity, the acceleration, or the bend angle of the at least one body segment is greater than the one or more thresholds.

13. The computing system of claim 10, wherein the one or more ergonomic zones are based at least in part on a number of instances in which the at least one of the velocity, the acceleration, or the bend angle associated with the at least one body segment exceeds the one or more thresholds during the measurement period.

14. The computing system of claim 10, wherein the ergonomic assessment garment is a smart garment constructed at least in part using electrically conductive yarns woven into a fabric structure of the ergonomic assessment garment.

15. A computer-implemented method of determining an ergonomic assessment associated with a user, the method comprising:

receiving, by one or more computing devices, sensor data from one or more sensors during a measurement period, the one or more sensors implemented with an ergonomic assessment garment worn by the user;

determining, by the one or more computing devices, corporeal data associated with at least one body segment of the user based at least in part on the sensor data, the corporeal data associated with a bend angle associated with the at least one body segment;

determining, by the one or more computing devices, one or more ergonomic zones based at least in part on the measurement period and the bend angle associated with the at least one body segment during the measurement period, wherein the one or more ergonomic zones are based at least in part on an amount of time during which the bend angle associated with the at least one body segment exceeds one or more thresholds during the measurement period; and determining, by the one or more computing devices, the ergonomic assessment associated with the user based at least in part on the corporeal data, the ergonomic assessment comprising an indication of one or more ergonomic zones associated with the user.

16. The computer-implemented method of claim 15, wherein the corporeal data comprises data associated with a timing of the bend angle of the at least one body segment relative to the one or more thresholds.

17. The computer-implemented method of claim 16, wherein determining, by the one or more computing devices, corporeal data for at least one body segment of the user comprises measuring the amount of time that the bend angle of the at least one body segment is greater than the one or more thresholds.

18. The computer-implemented method of claim 15, wherein the one or more ergonomic zones are based at least in part on a number of instances in which the bend angle associated with the at least one body segment exceeds the one or more thresholds during the measurement period.

19. The computer-implemented method of claim 15, wherein the corporeal data additionally comprises data associated with a range of motion of the at least one body segment.

20. The computer-implemented method of claim 15, wherein the ergonomic assessment garment is a smart garment constructed at least in part using electrically conductive yarns woven into a fabric structure of the ergonomic assessment garment.

\* \* \* \* \*